United States Patent
Yang et al.

(10) Patent No.: US 12,377,030 B2
(45) Date of Patent: Aug. 5, 2025

(54) LOW VISCOSITY, HIGH POLYOL SELF-FOAMING COMPOSITION

(71) Applicant: Conopco, Inc., Englewood Cliffs, NJ (US)

(72) Inventors: Lin Yang, Woodbridge, CT (US); Sheng Liang Tsaur, Norwood, NJ (US); Kevin David Hermanson, Woodbridge, CT (US)

(73) Assignee: Conopco, Inc., Hoboken, NJ (US)

( * ) Notice: Subject to any disclaimer, the term of this patent is extended or adjusted under 35 U.S.C. 154(b) by 624 days.

(21) Appl. No.: 16/606,804

(22) PCT Filed: May 4, 2018

(86) PCT No.: PCT/EP2018/061612
§ 371 (c)(1),
(2) Date: Oct. 21, 2019

(87) PCT Pub. No.: WO2018/206463
PCT Pub. Date: Nov. 15, 2018

(65) Prior Publication Data
US 2020/0383889 A1    Dec. 10, 2020

(30) Foreign Application Priority Data

May 10, 2017   (EP) .................................. 17170458

(51) Int. Cl.
*A61K 8/34*     (2006.01)
*A61K 8/04*     (2006.01)
(Continued)

(52) U.S. Cl.
CPC ............. *A61K 8/345* (2013.01); *A61K 8/046* (2013.01); *A61K 8/44* (2013.01); *A61K 8/442* (2013.01);
(Continued)

(58) Field of Classification Search
None
See application file for complete search history.

(56) References Cited

U.S. PATENT DOCUMENTS

2002/0070238 A1   6/2002   Pritchett et al.
2002/0122772 A1   9/2002   Lukenbach et al.
(Continued)

FOREIGN PATENT DOCUMENTS

CN   102209518   10/2011
CN   104257521   1/2015
(Continued)

OTHER PUBLICATIONS

Anonymous; Physical Properties of Glycerine and Its Solutions; ACI Science; 1967; pp. 1-27; XP055380469; retrieved from the internet: http://www.aciscience.org/docs/physical_properties_of_glycerine_and_its_solutions.pdf.
(Continued)

*Primary Examiner* — Sin J Lee
(74) *Attorney, Agent, or Firm* — Krista J. Aiello

(57) ABSTRACT

The invention provides high viscosity, low polyol compositions. By using surfactant system wherein 50% or more of the surfactant system comprises a surfactant of defined $V_h/I_c a_o$ value, it is possible to provide such composition having good foam appearance. If surfactants of such value are not used, the high polyol, low viscosity composition have "bad" foam attributes (not "self-foaming"), when measured for example after pumping through mechanical pump (composition has 0 to 0.5% propellant gel or gas).

10 Claims, 1 Drawing Sheet

Foam generated using a pump

Good foam
(9% Glutamate/CAPB
50% glycerin)
(A)

Bad foam
(3% SLES/CAPB 20% glycerin)
(B)

Bad foam
(9% Glutamate/CAPB
70% glycerin)
(C)

(51) Int. Cl.
    *A61K 8/44*     (2006.01)
    *A61K 8/46*     (2006.01)
    *A61K 8/60*     (2006.01)
    *A61Q 19/00*     (2006.01)
    *A61Q 19/10*     (2006.01)

(52) U.S. Cl.
    CPC .............. *A61K 8/466* (2013.01); *A61K 8/602* (2013.01); *A61Q 19/007* (2013.01); *A61Q 19/10* (2013.01)

(56) References Cited

U.S. PATENT DOCUMENTS

| | | | |
|---|---|---|---|
| 2003/0083210 | A1 | 5/2003 | Goldberg et al. |
| 2006/0217283 | A1 | 9/2006 | De Salvert et al. |
| 2008/0008672 | A1 | 1/2008 | Tobita |
| 2011/0182826 | A1* | 7/2011 | Boyke .................. A61K 8/35 424/10.3 |
| 2013/0032614 | A1* | 2/2013 | Babikian ............. B01F 13/1016 222/190 |
| 2015/0093348 | A1 | 4/2015 | Sato et al. |

FOREIGN PATENT DOCUMENTS

| | | |
|---|---|---|
| CN | 104661636 | 5/2015 |
| CN | 106491381 | 3/2017 |
| EP | 1029532 | 8/2000 |
| EP | 2740467 | 6/2014 |
| JP | 2006104149 | 4/2006 |
| JP | 2006183039 | 7/2006 |
| JP | 2006193549 | 7/2006 |
| JP | 2010059247 | 3/2010 |
| JP | 2011140464 | 7/2011 |
| JP | 2011148772 | 8/2011 |
| JP | 2014024875 | 2/2014 |
| JP | 2015526451 | 9/2015 |
| WO | WO2010056233 | 5/2010 |
| WO | WO2014029711 | 2/2014 |
| WO | WO2015156117 | 10/2015 |
| WO | WO2016093089 | 6/2016 |
| WO | WO2018054743 | 3/2018 |

OTHER PUBLICATIONS

Cleansing Foam; Mintel GNPD; 2011; pp. 1-2; XP002771027; China.
IPRP2 in PCTEP2018061612; Apr. 10, 2019; World Intellectual Property Org. (WIPO).
Search Report and Written Opinion in EP17170458; Jul. 3, 2017.
Search Report and Written Opinion in PCTEP2018061612.
Notice of Opposition in EP18722056 (3621578); Nov. 17, 2022; with English translation; European Patent Office (EPO).
Dipropylenglycole; Wikipedia; Nov. 10, 2022; pp. 1-4, with English translation, Retrieved from the Internet: URL: https://de.wikipedia.org/wiki/Dipropylenglycole; Germany.
Rompp Chemielexikon; Compound belonging to the group of the polyols; Glycerin; 2019; pp. 1-4, with English translation, Retrieved from the Internet: URL: https://roempp.thieme.de/lexicon/RD-07-01466; Germany.
Carl Roth; 1,3-Butanediol ≥ 99%, for synthesis; Safety Data Sheet; Feb. 21, 2017; pp. 1-11; Germany.

\* cited by examiner

Foam generated using a pump
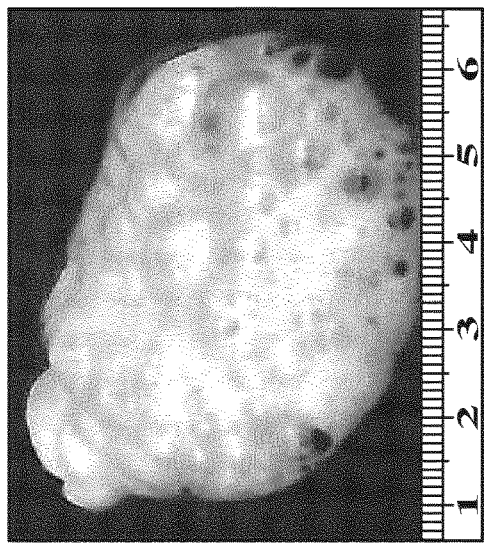
(A) Good foam
(9% Glutamate/CAPB 50% glycerin)
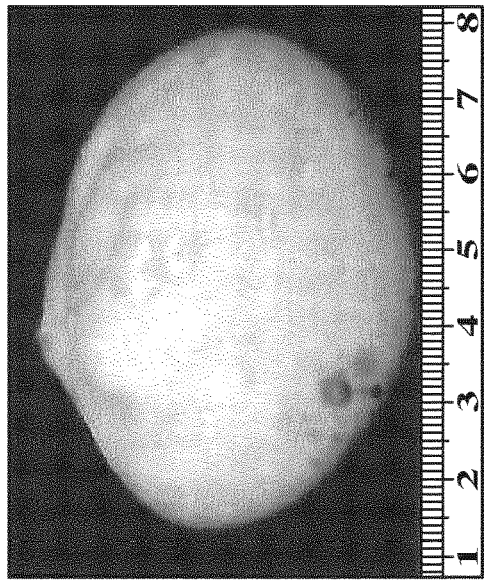
(B) Bad foam
(3% SLES/CAPB 20% glycerin)
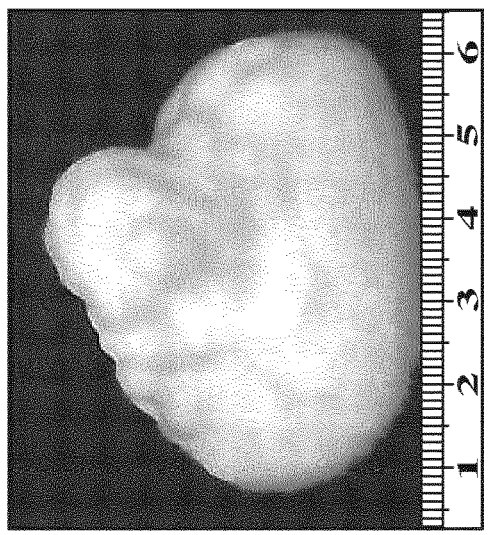
(C) Bad foam
(9% Glutamate/CAPB 70% glycerin)

LOW VISCOSITY, HIGH POLYOL SELF-FOAMING COMPOSITION

CROSS REFERENCE TO RELATED APPLICATIONS

The present application is a U.S. National Phase Application under 35 U.S.C. § 371 of International Application No. PCT/EP2018/061612, filed on May 4, 2018, which claims priority to European Patent Application No. 17170458.8, filed on May 10, 2017, the contents of which are incorporated herein in their entireties.

FIELD OF THE INVENTION

The present invention relates to high polyol, self-foaming, low viscosity compositions.

BACKGROUND OF THE INVENTION

Self-foaming compositions are known. Typically, delivery of foam is accomplished by using an air propulsion system such as, for example, air propelled containers; or by using a propellant gas or gases. Applicants are not aware of low viscosity, high polyol systems where it is recognized that at least 50% of at least one surfactant in the system must have defined value of $V_h/I_c a_o$ (where $V_h$ stands for the volume of the hydrophobic groups in the micellar core, $I_c$ is the length of the hydrophobic groups in the micellar core, and $a_o$ is the cross-sectional area occupied by the hydrophilic group at the micelle-solution interface) to ensure self-foaming compositions, as defined. Specifically, surfactants having $V_h/I_c a_o$ value of 0.1 to 0.25 must comprise 50% or more of the surfactant system.

Another way of delivering foam is through the use of micro-emulsions such as, for example, the oil-in-water emulsion disclosed in U.S. Publication No. 2006/0217283 to De Salvert et al. Foaming is achieved through a mixture of alkylpolyglucoside and at least one amphoteric surfactant and no propellant gas is used in the composition. The compositions are for topical application (e.g., cosmetics) and are intended, it seems, primarily as thick creams which have quite high viscosities (¶0033). Low viscosity, high polyol systems (for self-foaming compositions) are not disclosed.

U.S. Publication No. 2015/0093348 to Sato et al. discloses oil-in-water emulsions of relatively low viscosity (unlike, for example, traditional shampoos which have typically much higher viscosity) wherein foam is delivered via an air-propelled foaming appliance (¶0022). High polyol, low viscosity compositions comprising surfactant system wherein surfactant of a defined $V_h/I_c a_o$ value comprises 50% or more of the surfactant system are not disclosed.

U.S. Publication No. 2002/0122772 to Lukenbach et al. discloses self-foaming gels which comprise self-foaming agents, for example, pentane. The compositions are also high viscosity compositions.

U.S. Publication NO. 2003/0083210 to Goldberg et al. discloses compositions with self-foaming volatile agents and requires aerosol dispensing package. Compositions of our invention are not disclosed.

Some of the references disclose use of polyol, and specifically glycerine (Table 1 of U.S. Publication No. 2015/0093348 to Sato et al.), but exemplified levels are relatively low (2%). As noted, high polyol systems using surfactant system wherein surfactant of defined $V_h/I_c a_o$ value comprises 50% or more of surfactant system are not disclosed.

Applicants are unaware of any reference which discloses self-foaming compositions having high levels of polyol (20% to less than 70% by wt.), particularly glycerine, which are low viscosity compositions (viscosity less than 25 cps) having defined surfactants systems and which qualify as self-foamers when using 0 to 0.5% gel or gas propellant. Preferably, compositions of our invention are obtained in the substantial absence of self-foaming volatile agents. Rather, the foam of compositions of our invention is enhanced by using surfactant system wherein 50% or more, preferably 51 to 100% or more, preferably 60 to 100% of surfactant system comprises surfactant of $V_h/I_c a_o$ value of 0.1 to 0.25, preferably 0.1 to 0.225.

In applicants co-pending application, EP16190191.3, applicants disclose high glycerine compositions (containing 40 to 90% glycerine) comprising a surfactant system which in turn comprises N-acyl derivatives of dicarboxylic or mono-carboxylic amino acids. The present application is specific to self-foaming compositions which have specific low viscosity and in which foaming is enhanced by the selection of surfactant systems wherein 50 to 100%, preferably 51 to 100% of surfactant system comprises surfactant of defined $V_h/I_c a_o$ value. This is unrecognized in applicant's previous application. Preferably, the foaming is achieved in the substantial absence (0 to 0.5%, preferably 0 to 0.1%, more preferably, 0 to 0.01%, more preferably absent altogether) of self-foaming volatile agents (e.g., propellant gas or gases).

BRIEF DESCRIPTION OF THE INVENTION

The present invention relates to self-foaming compositions comprising:
1) greater than 20% to less than 70% polyol (e.g., glycerine);
2) wherein viscosity of the formulation is less than 25 cP; wherein
3) greater than 0.75 to 25% by wt., preferably 1.0 to 20%, more preferably 1.5 to 20% by wt. of a surfactant system (e.g., total surfactant level is 0.75 to 25% by wt.) comprises a surfactant selected from the group consisting of anionic surfactants, non-ionic surfactants, amphoteric surfactants, zwitterionic surfactants, cationic surfactants and mixtures thereof, wherein 50% or more, preferably 51% or more of the surfactant in the surfactant system comprises surfactant of $V_h/I_c a_o$ value (where $V_h$ is the volume of the hydrophobic groups in the micellar core, i.e., the "hydrophobic volume of the surfactant molecule"; $I_c$ is the length of the hydrophobic group, i.e., the hydrophobic portion longest chain length; and $a_o$ is the cross-sectional area occupied by the hydrophillic group at the micelle-solution interface, i.e., the "area slice through the hydrophilic portion") having a value of 0.1 to 0.25, preferably 0.1 to 0.225.

Preferably, the composition provides foam that qualifies as "self-foam" as assessed visually using methodology described below.

Because of high levels of polyol, preferably glycerine, used, compositions of this invention provide excellent hydration. Skin hydration can be measured using skin conductance values obtained as defined in the protocol. Although typically a conductance value (measured in micro seconds) greater than 1000, preferably greater than 1100, more preferably 1200 and greater, is considered to define excellent hydration, values can vary depending on population total, season of the year, etc. However, relative to compositions with no glycerine (replaced by water), compositions have measured conductance values at least 20%, preferably at least 30% higher, as measured in the clinical procedure for glycerine rich cleansers described in the protocol.

The foam is measured using foaming pump where no self-foaming volatile agents (e.g., propellants) are used. It should be understood that such agents may be used but are not required to obtain the visually observed "self-foams" of the invention.

That is, it is the compositions themselves which provide "self-foaming" attributes when viewed after pumping through a foaming pump as defined in the protocol.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. The use of and/or indicates that any one from the list can be chosen individually, or any combination from the list can be chosen.

For the avoidance of doubt, the word "comprising" is intended to mean "including" but not necessarily "consisting of" or "composed of." In other words, the listed steps or options need not be exhaustive.

Unless indicated otherwise, all percentages for amount or amounts of ingredients used are to be understood to be percentages by weight based on the active weight of the material in the total weight of the composition, which total is 100%.

The disclosure of the invention as found herein is considered to cover all embodiments as found in the claims as being multiply dependent on each other irrespective of the fact that the claims may be found without multiple dependency or redundancy.

The present invention related to self-foaming composition comprising:
1) greater than 20% to less than 70% polyol (e.g., glycerine);
2) wherein viscosity of the formulation is less than 25 cP (while not wishing to be bound by theory, believed responsible for enhanced foaming); wherein it has been found that, if a surfactant comprising 50% or more of the surfactant system is defined by a specific value which we have defined ($V_h/I_c a_o$ where $V_h$, $I_c$ and $a_o$ are defined above), then it is surprisingly found possible to maintain a composition which simultaneously:
    a) maintains desired low viscosity value (for foaming and for pumpability);
    b) comprises high polyol concentration (greater than 20% to less than 70%, preferably 20 to 65%, more preferably 20 to 60% by wt.); high glycerine values are desirable because they provide greater moisturization while minimizing surfactant damage; and
    c) has good foaming (qualifies as "self-foaming" as defined below); foaming is of course another desirable attribute that signals cleansing activity to the consumer.

Polyol

As indicated, compositions of the invention comprise 20% to less than 70%, preferably 20 to 65% by wt., more preferably 20 to 60% by wt. polyol.

The polyol is most preferably a liquid polyol, such as preferably glycerine, propylene, glycol, polypropylene glycol and mixtures thereof. While glycerine is a preferred polyol, other polyols may be used. These include sorbitol, propylene, glycol, polypropylene glycol and mixtures thereof (including preferably mixture of one of these with glycerine). For example, solid polyol, e.g. sorbitol, may be present in combination with liquid polyol. Liquid polyol, preferably glycerine, is preferably present in an amount of 20% to less than 70%, preferably 20 to 65% by wt., more preferably 20 to 60% by wt. based on the weight of the composition. If only solid polyol is used and solid surfactant, the skilled person will understand that water is present in the composition to satisfy the viscosity range of the composition.

At levels used, the polyol provides enhanced moisturization, confirmed by measured conductance values of 1000 microseconds or greater; and/or by moisture enhancement (also using conductance values) of 20% or more relative to control compositions with no glycerine. Measurement of conductance is done as described in the protocol in the section relating to clinical procedure for glycerine rich cleansers. Using compositions of the Invention, applicants are able to provide high polyol levels in low viscosity compositions (good for pumping) while surprisingly maintaining superior foam characteristics (as defined by visual observation) after pumping through a foaming pump using defined material. The ability to maintain low viscosity (and have foam and pumping) using specific surfactant system was quite surprising. A "self-foaming" foam is one which is creamy (having small bubble size); wherein the stripes of the foam pile up (rather than collapse), and which maintains its shape for several (2-3) minutes; wherein the foam does not run nor spread on a flat surface. This can be observed in FIG. 1A. Examples of foam which is not visually a "self-foam" is seen from FIGS. 1B and 1C.

Surfactant

The compositions of the invention further comprise from greater than 0.75 to 25% by wt., preferably 1.5 to 25% by wt., more preferably 1.5 to 20% by wt. even more preferably of from 1.5 to 15 wt % and even more preferably of from 1.5 to 12 wt % of surfactant wherein 50% or more, preferably 51% or more of the total surfactant has a $V_h/I_c a_o$ value of 0.1 to 0.25, preferably 0.1 to 0.225. Surfactant is preferably selected from the group consisting of anionic surfactants, non-ionic surfactants, amphoteric surfactants, zwitterionic surfactants, cationic surfactants and mixtures thereof, wherein 50% or more, preferably 51% or more of the total surfactant has a $V_h/I_c a_o$ value of 0.1 to 0.25, preferably 0.1 to 0.225.

According to this equation, $V_h$ defines the volume of the hydrophobic groups in the micellar core and can also be referred to as the hydrophobic volume of the surfactant molecule. $I_c$ refers to the length of the hydrophobic group and refers to the longest chain length. Finally, $a_o$ refers to the cross-sectional areas occupied by the hydrophilic group and the interface of the micelle in solutions; this is the area slice through the hydrophilic portion.

The value can be calculated for a given surfactant using, for example, Molecular Modeling Pro® Software Revision 3.2, published by ChemSW® Inc. Typically, chemical structure is inputted and models well known to those skilled in the art are used to estimate $V_h$, $I_c$ and $a_o$.

Unexpectedly, applicants have found that when a surfactant having calculated value of $V_h/I_c a_o$ of 0.1 to 0.25 comprises 50% to 100%, preferably 51% to 100% in a composition having 20 to less than 70% polyol (at 70% or more, the viscosity becomes higher than desired), then the composition obtains visually desirable "self-foam" foam (qualifies as "self-foam" as observed according to attributes set forth in the protocol and seen in FIG. 1).

Thus, for example, a sodium glutamate (having calculated value of about 0.169; see Table 1) or alkyl glucoside (having calculated value of 0.194; see Table 1), when used at level 50% greater in composition having 20% to less than 70% polyol, will qualify as "self-foam". However, as seen in Tables 6 and 7, using essentially identical formulations, where surfactant is SLES 1 EO (with calculated value of 0.316), none of the examples qualify as self-foaming foams.

Preferred surfactants which may be used (if used at levels of 50% and higher) are sultaines, betaines, alkyl taurates, alkyl glutamates and glycinates, alkyl isethionates, alkyl glucosides, and alkyl amphoacetates. Particularly preferred are glutamates, glycinates and isehtionases.

Typically, the alkyl chain length of surfactants used and which are calculated are C8 to C16, preferably, 010 to C14, and most preferably C12, for example, C12 chain length glucoside. Of course, if chain length is longer and calculated $V_h/I_c a_o$ value falls in the range of 0.1 to 25, the surfactant still falls within claims of the invention.

While not wishing to be bound by theory, the calculated values (see Table 1) are believed to represent how the surfactant packs and how water drains from the film forming in pumps through which the surfactant pass.

In another aspect, the invention relates to a method of providing self-foaming foam (as defined above) in compositions comprising 20 to less than 70% polyol which method comprises formulating with use of 50% or more surfactant having $V_h/I_c a_o$ value of 0.1 to 0.25.

Viscosity

The viscosity of the composition is 25 cp or less. Such a viscosity is needed to provide the self-foaming character of the composition. To create the foam, the composition is for example pumped through a mesh in a pump device, for example by a hand pump. The skilled person will be aware of the general thickening effect of polyol or surfactant in cleansing compositions. In the context of the present invention, a lower level of surfactant may allow for a higher level of polyol, whereas a lower level of polyol may allow for a higher level of surfactant, within the indicated ranges, to satisfy the viscosity requirement. It may be preferred that the composition further comprises water. Viscosity measurements are carried out with a standard RV Brookfield viscometer fitted with spindle size 4, rotating at 20 rpm for 30 seconds before reading. Viscosity is measured at room temperature. Preferred range is from 23 to 27 degrees C., preferably 24 to 26 degrees C. and most preferably 25 degrees C.

The invention further relates to a method to manufacture a foam, the method comprising the steps of:
a) providing a composition according to any one of the preceding claims,
b) pumping the composition through a mesh in a foaming pump, preferably through a 200/100 mesh,
to result in in a foam.

In a further aspect, the invention relates to the use of a surfactant defined by a $V_h/I_c a_o$ value of 0.1 to 0.25, wherein NA is the volume of the hydrophobic groups of the micellar core, $I_c$ is the length of the hydrophobic group and $a_o$ is the cross-sectional area occupied by the hydrophilic group at the micelle-solution interface, in a composition comprising 1.5% to 25% of total surfactant (wt % on total resulting composition) and 20% to less than 70% polyol (wt % on total resulting composition), wherein the surfactant defined by a $V_h/I_c a_o$ value of 0.1 to 0.25 is present in an amount of 50% or more of the total surfactant in the resulting composition and wherein the resulting composition comprises no more than 0 to 0.5% propellant gel or gas and wherein the viscosity of the resulting composition is 25 cP or less, measured at 25° C.

FIGURES

FIG. 1 is a photo of what good versus bad foam looks like when visually observed, following protocol for observing foam quality.

EXAMPLES

Experimental Procedures
Protocol
Clinical Procedure for Glycerin Rich Cleanser—Measurement of Hydration Using Skin Conductance Subjects are 18-65 years old male or females, having slightly dry skin on forearms (visual grade of 0.5-2 on a 0-6 dryness grading scale). Minimum 30 subjects are needed to complete the study. Subjects should have even dryness score on both arms (within a grade of 0.5). Six sites on forearms (3 sites on each arm) are tested. This clinical study is a randomized, evaluator-blind/subject-blind controlled normal wash study and with minimum 30 subjects is considered statistically significant.

Controlled washes were conducted twice daily on each site for 4 weeks (27 days), with 4 to 5 hours apart between the two washes in a day. A five day conditioning phase was done by washing with a commercial soap bar comprising sodium tallowate, sodium cocoate, cocamidopropyl betaine twice daily (–5 day starting). On Days 1, 7, 14, 21, and 28, morning visits before wash, the subjects were acclimated in an environmentally controlled room maintained at 66.6° F. to 71.9° F. and at 24% to 55% relative humidity for at least 30 minutes prior to instrumental assessments.

Skin conductance was measured using Skicon (200EX with MT8C probe; I.B.S., Co., Ltd.). Triplicate Skicon readings were taken from each site. Data presented is the mean change from baseline. A skin conductance value of 1000 microseconds or greater is indicative of good moisturization. While the absolute values can vary depending on population total or the season of the year, the moisture may also be confirmed by improvement of 20% or more in conductance value relative to control composition with no glycerin (replaced by water).

During the study period, subjects were asked to avoid using any skin care products on testing sites (forearms). They were required to take evening showers every day with a commercial soap bar comprising sodium lauroyl isethionate, stearic acid, sodium tallowate or sodium palmitate, lauric acid (e.g., Dove® bar from Unilever), but to avoid applying any cleansing product on arms (it is acceptable if residual solution flows down on treated site (e.g., forearm) when showering).

Value of $V_h/I_c a_0$: The value of $V_h/I_c a_0$ has been used routinely to predict the micellar structure for surfactant in aqueous solution, where $V_h$ stands for the volume of the hydrophobic groups in the micellar core, $I_c$ is the length of the hydrophobic group in the core, and $a_0$ is the cross-sectional area occupied by the hydrophilic group at the micelle-solution interface. Molecular modeling pro™ revision 3.2 (published by ChemSW™ Inc.) was used to calculate those parameters of a surfactant based on the structure of the surfactant. Value of calculated $V_h/I_c a_0$ for various surfactants was listed in Table 1.

TABLE 1

| | Value of $V_h/I_c a_0$ of surfactant | | | |
|---|---|---|---|---|
| | hydrophobic volume $V_h$ (Å^3) | area of slice through hydrophilic portion $a_0$ (Å^2) | Hydrophobic portion longest chain length $I_c$ (Å) | $V_h/I_c a_0$ |
| cocamidopropyl hydroxysultaine (CAPHs) | 105.18 | 89.274 | 14.634 | 0.0805 |
| cocamidopropyl betaine (CAPB) | 105.18 | 84.11 | 14.63 | 0.0854 |
| Sodium methyl lauroyl taurate | 105.18 | 47.22 | 14.63 | 0.15221 |
| Sodium lauroyl glutamate | 111.72 | 45.13 | 14.63 | 0.169 |
| Sodium lauroyl isethionate | 111.72 | 43.8 | 14.46 | 0.176 |
| Alkyl glucoside | 1115.04 | 37.37 | 15.87 | 0.194 |
| Sodium lauroyl glycinate | 105.175 | 36.72 | 14.63 | 0.196 |
| Sodium lauroamphoacetate | 101.92 | 34.98 | 14.76 | 0.1974 |
| Sodium lauroyl sarcosinate | 105.18 | 27.403 | 13.58 | 0.283 |
| Mono alkyl phosphate (MAPs) | 111.78 | 24.45 | 15.87 | 0.288 |
| Sodium lauryl sulfate (SDS) | 105 | 23.9 | 14.96 | 0.293 |
| Sodium laureth sulfate (SLES.1EO) | 115 | 22.95 | 15.80 | 0.316 |
| Sodium Laurate (NaL) | 105.17 | 14.12 | 14.63 | 0.5089 |

Like most surfactants commonly used, the alkyl chain length of the measured surfactants of table 1 is C12 (with C10 or C14 mainly as residual in production of surfactant). So, alkyl glucoside used here, for example, was C12 glucoside.

Å (angstrom): unit of length.

Viscosity Measurement of Formulation: Measurements were carried out with a standard RV Brookfield viscometer fitted with spindle size 4, rotating at 20 rpm for 30 sec before taking reading. The spindle was positioned to be completely immersed by the samples. For each sample, the measurement was repeated 3 times and the average of these 3 readings are reported as viscosity of the sample. Viscosity was measured at 25 degrees C.

Foam quality for self-foamer: In this invention, foam was generated using foaming pump, instead of gas propellants. The foaming pump used is from Albea Thomaston Inc (60 electric avenue, Thomaston, CT 67787), 200/100 mesh (sample ID 41350). The foam was generated as the following: a clean pump with a bottle that containing said formulation was pushed 10 times and the foam generated was discarded. Then the pump was pushed 6 times consecutively with the bottle tilted and aiming at one position on a flat surface. The foam on that flat surface was then assessed visually. A foam qualifies for self-foamer will be creamy, no visible large bubbles, the stripes of the foam piles up and maintains its shape for a few minutes, and the foam is not running/spreading on the flat surface. An example of such foam will be FIG. 1A. The foam generated by above described method that does not qualify as self-foamer will be visibly containing of numerous large bubbles, the stripes of the foam does not maintain its shape—rather the foam is watery and running, or no continuous stripes coming out of the pump (such as FIG. 1B and FIG. 1C).

EXAMPLES

Example 1

Cleanser Composition with Glycerin Content within the Range of 20%<Glycerin Concentration<70% for Superior Skin Hydration Benefits

TABLE 2

| | Example 1-1 | Example 1-2 | Example 1-3 | Comparative 1-A | Comparative 1-B |
|---|---|---|---|---|---|
| Glutamate (sodium lauroyl glutamate) | 6.75% | 6.75% | 6.75% | 6.75% | 0% |
| CAPB (cocoamidipropyl betaine) | 2.75% | 2.75% | 2.75% | 2.75% | 0% |
| Water | To balance | To balance | To balance | To balance | 100% |
| Glycerin | 20% | 50% | 70% | 0% | 0% |

TABLE 3

| | Conductance Values (measured in μ seconds) |
|---|---|
| Example 1-1 | 1276 |
| Example 1-2 | 1443 |
| Example 1-3 | 1402 |
| Comparative 1-A | 919 |
| Comparative 1-B | 204 |

From Tables 2 and 3, it can be seen that compositions of the invention require between 20 and 70% polyol (preferably glycerin) to provide superior hydration benefits (defined as having conductance values of 1000 micro seconds or greater).

Example 2

Glutamate/CAPB (3:1) Surfactant Blend for Self-Foamer: Surfactant Concentration at 50% Glycerin Level (pH 6.5)

TABLE 4

| | Example 2-1 | Example 2-2 | Example 2-3 | Example 2-4 | Example 2-5 | Comparative 2-A | Comparative 2-B |
|---|---|---|---|---|---|---|---|
| Glutamate (sodium lauroyl glutamate) | 11.25% | 6.75% | 5.625% | 2.25% | 1.125% | 0.5625% | 0.375% |
| CAPB (cocoamidipropyl betaine) | 3.75% | 2.75% | 1.875% | 0.75% | 0.375% | 0.1875% | 0.125% |
| (total surfactant level) | (15%) | (9%) | (7.5%) | (3%) | (1.5%) | (0.75%) | (0.5%) |
| Water | To balance | To balance | To balance | To balance | To balance | To balance | To balance |
| Glycerin | 50% | 50% | 50% | 50% | 50% | 50% | 50% |
| Viscosity (cP) | <10 | <10 | <10 | <10 | <10 | <10 | <10 |
| Qualifies as self-foamer | yes | yes | yes | yes | yes | no | no |

From Example 2, it can be seen (from Comparative 2-A, 2-B) that, when glycerin level is 50% in formulation, total level of surfactant (Glutamate/CAPB 3:1) must be greater than 0.75%, preferably 1.5 to 25% of surfactant system to be defined as composition which is self-foaming.

Example 3

Glutamate/CAPB (3:1) Surfactant Blend for Self-Foamer: surfactant Concentration at 20% Glycerin Level (pH 6.5)

TABLE 5

| | Example 3-1 | Example 3-2 | Example 3-3 | Example 3-4 | Example 3-5 | Comparative 3-A | Comparative 3-B |
|---|---|---|---|---|---|---|---|
| Glutamate (sodium lauroyl glutamate) | 11.25% | 6.75% | 5.625% | 2.25% | 1.125% | 0.5625% | 0.375% |
| CAPB (cocoamidipropyl betaine) | 3.75% | 2.75% | 1.875% | 0.75% | 0.375% | 0.1875% | 0.125% |
| (total surfactant level) | (15%) | (9%) | (7.5%) | (3%) | (1.5%) | (0.75%) | (0.5%) |
| Water | To balance | To balance | To balance | To balance | To balance | To balance | To balance |
| Glycerin | 20% | 20% | 20% | 20% | 20% | 20% | 20% |
| Viscosity (cP) | <10 | <10 | <10 | <10 | <10 | <10 | <10 |
| Qualifies as self-foamer | yes | yes | yes | yes | yes | no | no |

Again, from Example 3, it can be seen (from Comparative 3-A, 3-B) that, when glycerin level is 20% glycerin, total level of surfactant (Glutamate/CAPB 3:1) must be greater than 0.75%, preferably 1.5 to 25% of surfactant system to be defined as composition which is self-foaming.

Example 4

9% Glutamate/CAPB (3:1) Surfactant Blend for Self-Foamer: Glycerin Level (pH 6.5)

TABLE 6

|  | Example 4-1 | Example 4-2 | Example 4-3 | Comparative 4-A |
|---|---|---|---|---|
| Glutamate (sodium lauroyl glutamate) | 6.75% | 6.75% | 6.75% | 6.75% |
| CAPB (cocoamidipropyl betaine) | 2.75% | 2.75% | 2.75% | 2.75% |
| (total surfactant level) | (9%) | (9%) | (9%) | (9%) |
| Water | To balance | To balance | To balance | To balance |
| Glycerin | 20% | 50% | 60% | 70% |
| Viscosity (cP) | <10 | <10 | 25 | 120 |
| Qualifies as self-foamer | yes | yes | yes | no |

Example 5

6% Glutamate/CAPB (3:1) Surfactant Blend for Self-Foamer: Glycerin Level (pH 6.5)

TABLE 7

|  | Example 5-1 | Example 5-2 | Example 5-3 | Comparative 5-A |
|---|---|---|---|---|
| Glutamate (sodium lauroyl glutamate) | 4.5% | 4.5% | 4.5% | 4.5% |
| CAPB (cocoamidipropyl betaine) | 1.5% | 1.5% | 1.5% | 1.5% |
| (total surfactant level) | (6%) | (6%) | (6%) | (6%) |
| Water | To balance | To balance | To balance | To balance |
| Glycerin | 20% | 50% | 60% | 70% |
| Viscosity (cP) | <10 | <10 | <10 | 90 |
| Qualifies as self-foamer | yes | yes | yes | no |

From Example 4 and Example 5, it can be seen (from Comparative 4-A and 5-A) that glycerin level must be less than 70%, preferably less than 65% to be defined as composition which is self-foaming. Another observation is formulation viscosity need to be less than 25 cP to be defined as composition which is self-foaming.

Example 6

SLES/CAPB (3:1) Surfactant Blend for Self-Foamer: Surfactant Concentration at 50% Glycerin Level (pH 6.5)

TABLE 8

|  | Comparative 6-A | Comparative 6-B | Comparative 6-C | Comparative 6-D | Comparative 6-E | Comparative 6-F |
|---|---|---|---|---|---|---|
| SLES.1EO (s) | 11.25% | 6.75% | 5.625% | 2.25% | 1.125% | 0.5625% |
| CAPB (cocoamidipropyl betaine) | 3.75% | 2.75% | 1.875% | 0.75% | 0.375% | 0.1875% |
| (total surfactant level) | (15%) | (9%) | (7.5%) | (3%) | (1.5%) | (0.75%) |
| Water | To balance | To balance | To balance | To balance | To balance | To balance |
| Glycerin | 50% | 50% | 50% | 50% | 50% | 50% |
| Viscosity (cP) | 670 | 15 | <10 | <10 | <10 | <10 |
| Qualifies as self-foamer | No | No | No | No | No | No |

Example 7

SLES/CAPB (3:1) Surfactant Blend for
Self-Foamer: Surfactant Concentration at 20%
Glycerin Level (pH 6.5)

TABLE 9

|  | Comparative 7-A | Comparative 7-B | Comparative 7-C | Comparative 7-D | Comparative 7-E | Comparative 7-F |
|---|---|---|---|---|---|---|
| SLES.1EO (sodium laureth sulfate) | 11.25% | 6.75% | 5.625% | 2.25% | 1.125% | 0.5625% |
| CAPB (cocoamidipropyl betaine) | 3.75% | 2.75% | 1.875% | 0.75% | 0.375% | 0.1875% |
| (total surfactant level) | (15%) | (9%) | (7.5%) | (3%) | (1.5%) | (0.75%) |
| Water | To balance | To balance | To balance | To balance | To balance | To balance |
| Glycerin | 20% | 20% | 20% | 20% | 20% | 20% |
| Viscosity (cP) | 1620 | 10 | <10 | <10 | <10 | <10 |
| Qualifies as self-foamer | No | No | No | No | No | No |

From Table 8 and Table 9, it was observed that when SLES/CAPB (3:1) surfactant blend was used, none of the tested formulations will qualify as self-foaming. Note that glycerin level, or formulation viscosity, are similar to examples 4 & 5. While not wish to be bound by theory, the selection of surfactant blend is believed to determine whether a formulation containing high glycerin will qualify for self-foamer. SLES, the surfactant that accounts for more than 50% in the total surfactant blend in example 6 & 7, has $V_h/I_c a_0$ larger than 0.25 (where $V_h$ stands for the volume of the hydrophobic groups in the micellar core, $I_c$ is the length of the hydrophobic group in the core, and $a_0$ is the cross-sectional area occupied by the hydrophilic group at the micelle-solution interface).

Example 8

APG Surfactant for Self-Foamer: Surfactant
Concentration at 50% Glycerin Level (pH 7)

TABLE 10

|  | Example 8-1 | Example 8-2 | Example 8-3 | Example 8-4 | Example 8-5 | Comparative 8-A | Comparative 8-B |
|---|---|---|---|---|---|---|---|
| Alkyl*glucoside (APG) | 15% | 9% | 7.5% | 3% | 1.5% | 0.75% | 0.5% |
| (total surfactant level) | (15%) | (9%) | (7.5%) | (3%) | (1.5%) | (0.75%) | (0.5%) |
| Water | To balance | To balance | To balance | To balance | To balance | To balance | To balance |
| Glycerin | 50% | 50% | 50% | 50% | 50% | 50% | 50% |
| Viscosity (cP) | 10 | 10 | <10 | <10 | <10 | <10 | <10 |
| Qualifies as self-foamer | yes | yes | yes | yes | yes | no | no |

*As indicated, $V_h/I_c a_0$ value calculated was based on C12 glucoside

Example 9

APG Surfactant for Self-Foamer: Surfactant Concentration at 20% Glycerin Level (pH 7)

TABLE 11

|  | Example 9-1 | Example 9-2 | Example 9-3 | Example 9-4 | Example 9-5 | Comparative 9-A | Comparative 9-B |
|---|---|---|---|---|---|---|---|
| Alkyl* glucoside (APG) | 15% | 9% | 7.5% | 3% | 1.5% | 0.75% | 0.5% |
| (total surfactant level) | (15%) | (9%) | (7.5%) | (3%) | (1.5%) | (0.75%) | (0.5%) |
| Water | To balance | To balance | To balance | To balance | To balance | To balance | To balance |
| Glycerin | 20% | 20% | 20% | 20% | 20% | 20% | 20% |
| Viscosity (cP) | 10 | <10 | <10 | <10 | <10 | <10 | <10 |
| Qualifies as self-foamer | yes | yes | yes | yes | yes | no | no |

*Same as Table 9, as well as same for alkyl glucoside (C12) for Tables 10 and 11

TABLE 12

|  | Example 10-1 | Example 10-2 | Example 10-3 | Comparative 10-A |
|---|---|---|---|---|
| Alkyl glucoside (APG) | 6% | 6% | 6% | 6% |
| (total surfactant level) | (6%) | (6%) | (6%) | (6%) |
| Water | To balance | To balance | To balance | To balance |
| Glycerin | 20% | 50% | 60% | 70% |
| Viscosity (cP) | <10 | <10 | <10 | 70 |
| Qualifies as self-foamer | yes | yes | yes | no |

Example 11

9% APG Surfactant for Self-Foamer: Glycerin Level (pH 7)

TABLE 13

|  | Example 11-1 | Example 11-2 | Example 11-3 | Comparative 11-A |
|---|---|---|---|---|
| Alkyl glucoside (APG) | 9% | 9% | 9% | 9% |
| (total surfactant level) | (9%) | (9%) | (9%) | (9%) |
| Water | To balance | To balance | To balance | To balance |
| Glycerin | 20% | 50% | 60% | 70% |
| Viscosity (cP) | <10 | <10 | <10 | 80 |
| Qualifies as self-foamer | yes | yes | yes | no |

From Example 8, 9, 10 & 11, it was found that when another surfactant, APG, that has a $V_h/I_c a_0$ value smaller than 0.25, was used, again we see that minimum amount of surfactant is needed and that compositions have to have low viscosity to qualify as self-foaming compositions of our invention.

The invention claimed is:

1. A self-foaming composition comprising:
   a. 20 wt % to less than 70 wt % polyol; and
   b. 1.5 wt % to 9.5 wt % of total surfactant wherein 50 wt % or more of the total surfactant is a surfactant defined by a $V_h/I_c a_o$ value of 0.1 to 0.25, wherein $V_h$ is a volume of hydrophobic groups of a micellar core, $I_c$ is a length of the hydrophobic group and $a_o$ is a cross-sectional area occupied by a hydrophilic group at a micelle-solution interface; wherein the total surfactant is selected from the group consisting of sultaines, betaines, alkyl taurates, alkyl glutamates and glycinates, alkyl isethionate, alkyl glucosides, alkyl amphoacetate and mixtures thereof;

wherein viscosity of the composition is 25 cP or less, measured at 25° C.;

wherein the composition comprises no more than 0 to 0.5 wt % propellant gel or gas.

2. The composition according to claim 1, wherein the polyol is a liquid polyol.

3. The composition according to claim 2, wherein the liquid polyol is glycerine.

4. The composition according to claim 1 comprising 20 to less than 65 wt % polyol.

5. The composition according to claim 1, wherein 51 to 100 wt % of the total surfactant is the surfactant defined by a $V_h/I_c a_o$ value of 0.1 to 0.25.

6. The composition according to claim 1, wherein the alkyl taurates, alkyl glutamates and glycinates, alkyl isethionate, alkyl glucosides, and alkyl amphoacetate have an alkyl chain length of $C_8$ to $C_{16}$.

7. The composition according to claim 6, wherein the alkyl taurates, alkyl glutamates and glycinates, alkyl isethionate, alkyl glucosides, and alkyl amphoacetate have an alkyl chain length of $C_{10}$ to $C_{14}$.

8. The composition according to claim 7, wherein the alkyl taurates, alkyl glutamates and glycinates, alkyl isethionate, alkyl glucosides, and alkyl amphoacetate have an alkyl chain length of $C_{12}$.

9. A method to manufacture a foam, the method comprising the steps of:
   a) providing the composition according to claim 1,
   b) pumping the composition through a mesh in a foaming pump,
to result in a foam.

10. The method according to claim 9, wherein the mesh is a 200/100 mesh.

* * * * *